Figure 3:
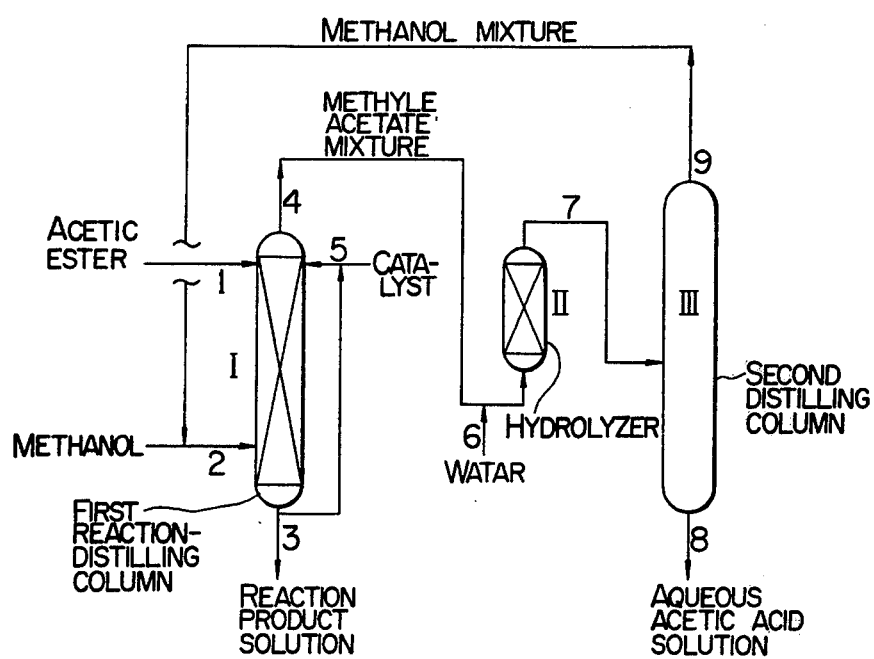

United States Patent [19]

Yoshida et al.

[11] 4,283,579
[45] Aug. 11, 1981

[54] PROCESS FOR PRODUCING DIOL

[75] Inventors: Yoshinori Yoshida, Yokohama; Hiroshi Oka, Tokyo, both of Japan

[73] Assignee: Japan Synthetic Rubber Co., Ltd., Tokyo, Japan

[21] Appl. No.: 72,991

[22] Filed: Sep. 6, 1979

[30] Foreign Application Priority Data

Sep. 7, 1978 [JP] Japan .................................. 53-109083

[51] Int. Cl.³ ........................ C07C 31/20; C07C 27/02
[52] U.S. Cl. ..................................... 568/857; 568/858
[58] Field of Search ................................ 568/858, 857

[56] References Cited

U.S. PATENT DOCUMENTS

| 3,776,948 | 12/1973 | Kleemann et al. | 568/858 |
|---|---|---|---|
| 3,880,939 | 4/1975 | Corn et al. | 568/858 |
| 3,965,152 | 6/1976 | Smith et al. | 568/858 |

FOREIGN PATENT DOCUMENTS 2430022 10/1975 Fed. Rep. of Germany ........... 568/858

Primary Examiner—Joseph E. Evans
Attorney, Agent, or Firm—Oblon, Fisher, Spivak, McClelland & Maier

[57] ABSTRACT

A process for producing a diol by reacting an acetic ester of butanediol or butenediol with methanol, which comprises (a) continuously feeding to a first reaction-distilling column from its upper part a liquid acetic ester of butanediol or butenediol, while continuously feeding methanol to said column from its lower part, to bring both feeds into counter current gas-liquid contact in the presence of an acidic or a basic catalyst, to allow both feeds to react, and withdrawing from the bottom a bottom stream comprising a diol as major constituent, (b) continuously feeding to a hydrolyzer the distillate obtained from said first reaction-distilling column containing methyl acetate as major constituent, thus bringing said distillate into contact with water or steam in the presence of an acidic catalyst to hydrolyze the methyl acetate, (c) then continuously feeding the hydrolysis product thus obtained from the hydrolyzer to a second distilling column, withdrawing a methyl acetate-containing methanol stream from the top of said second distilling column, and recycling said stream to the lower part of the first reaction-distilling column. According to this process, it is possible to leave out the conventional complicated procedure necessary for the separation of methanol and, hence, to save the labor required therefor.

20 Claims, 3 Drawing Figures

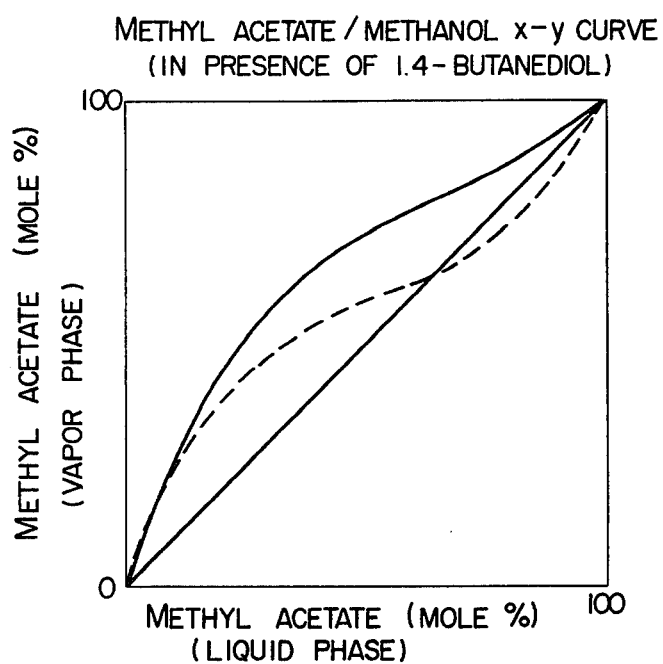
FIG. 1  METHYL ACETATE / METHANOL x-y CURVE
(IN PRESENCE OF 1.4-BUTANEDIOL)
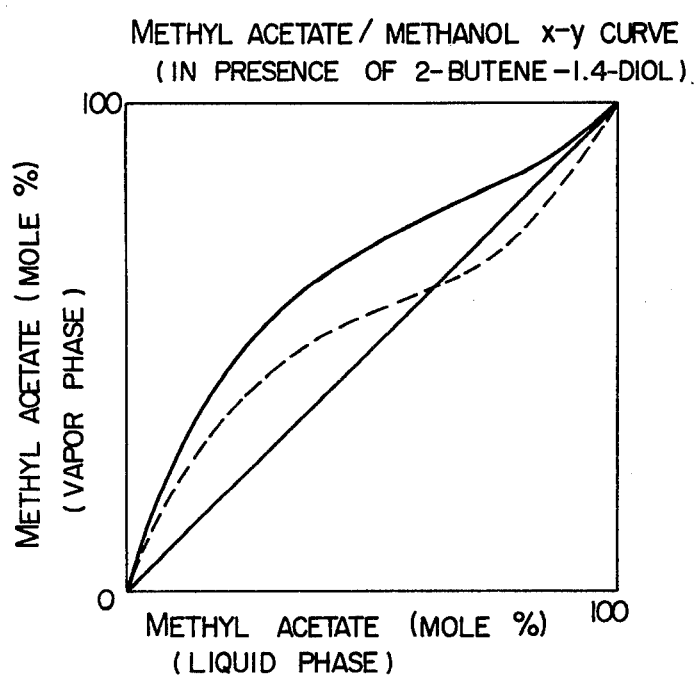
FIG. 2  METHYL ACETATE / METHANOL x-y CURVE
(IN PRESENCE OF 2-BUTENE-1.4-DIOL)

PROCESS FOR PRODUCING DIOL

This invention relates to a process for continuously producing a diol from the acetic ester thereof by transesterification with methanol. More particularly, it relates to a process for producing a diol by transesterification between the acetic ester of the diol and methanol, characterized by hydrolyzing methyl acetate which is obtained as a by-product along with the diol in said transesterification, then distilling the hydrolyzate to recover the methanol containing methyl acetate as the distillate, and using said distillate without any treatment again as the reactant in said transesterification.

The term "acetic ester of a diol" used herein means to include 1,2-diacetoxybutane, 1,4-diacetoxybutane, 3,4-diacetoxybutene-1, and 1,4-diacetoxybutene-2, and the term "diol" used herein means to include 1,2-butanediol, 1,4-butanediol, 1-butene-3,4-diol, and 2-butene-1,4-diol.

For the production of a diol from the acetic ester thereof by the elimination of the ester group, several methods have heretofore been known. For instance, there is a known method by which the above ester is hydrolyzed with a water soluble base solution. This method, however, has a disadvantage that one equivalent of acetic acid salt is produced from one equivalent of the ester, and hence, when the salt is treated with an inorganic acid to obtain and reuse acetic acid a large quantity of undesirable inorganic salt is formed. In another known method, an acidic catalyst is used in hydrolyzing the said ester. By this method is formed an equilibrium mixture containing the diol and large amounts of the monoacetate of the diol and unreacted diacetate of the diol. Separation of the mixture into the respective components required complicated procedures and a large expenditure of thermal energy.

On the other hand, transesterification with an acidic or basic catalyst is known and it is also known that a diol is formed quantitatively thereby. In particular, the transesterification with methanol is considered to be most preferable. The methyl acetate produced as a by-product in the transesterification between the acetic ester of a diol and methanol is generally converted by hydrolysis into methanol and acetic acid, both being reused.

This method for the production of a diol by transesterification with methanol, however, has also the following problems:

In the hydrolysis of methyl acetate, the following equilibrium relation, $$\frac{[\text{methanol}][\text{acetic acid}]}{[\text{methyl acetate}][\text{water}]} = K,$$

requires a large amount of water for allowing the hydrolysis reaction to proceed. Also, a great thermal load must be borne in distillation and other treatments in order to isolate methanol, which is one of the starting materials for the transesterification, from the four-component reaction mixture after the hydrolysis consisting of methyl acetate, methanol, water and acetic acid, because methyl acetate and methanol form an azeotrope. If, on the other hand, the methanol is not isolated from this azeotrope, and fresh methanol is fed, the compolicated step of separating methanol from the azeotrope and the accompanying expenditure of much labor could be avoided, but this is disadvantageous in the following respects: The amount of methanol used becomes much larger than the theoretical amount of methanol to be consumed in the transesterification, whereby an increased amount of thermal energy and an increased volume of equipment become necessary to treat such a large amount of methanol, and the advantage is impaired that the diol is produced quantitatively by the transesterification. Therefore, there has been desired a commercially beneficial method for producing a diol by transesterification including treatment of methyl acetate produced as a by-product.

In order to solve the aforementioned problems, the present inventors have conducted extensive studies on a commercially advantageous process for producing a diol by transesterification between the acetic ester of the diol and methanol and have, as a result, found that when methyl acetate-containing methanol is withdrawn in place of taking out high-purity methanol, from the reaction mixture obtained by the hydrolysis of the methyl acetate obtained as a by-product and is used, without any treatment, as the starting material for the transesterification, the diol is obtained quantitatively without any interference with the progress of reaction, and in addition, the use of the methyl acetate-containing methanol as the starting material enables one to obtain from the top of the reaction-distilling column a methyl acetate-methanol fraction richer in methyl acetate content than the methyl acetate-methanol azeotropic mixture (65:35 molar ratio), and hence, the amount of water used in the hydrolysis of methyl acetate can be reduced.

An object of this invention is to provide an improvement in a process for producing continuously a diol in a reaction-distilling column by transesterification between the acetic ester of the diol and methanol, which improvement comprises hydrolyzing the distillate containing methyl acetate as major constituent obtained form the top of the column and reusing the hydrolyzate as said methanol.

Another object of this invention is to leave out a complicated step of methanol-isolation and the labor necessary therefor in a process for continuously producing a diol.

Other objects and advantages of this invention will become apparent from the following description.

According to this invention, there is provided a process for producing a diol by reacting an acetic ester of butanediol or butenediol with methanol, which comprises (a) continuously feeding to a first reaction-distilling column from an upper part thereof a liquid acetic ester of a butanediol or butenediol, while continuously feeding methanol to the said column from a lower part thereof, to bring both feeds into counter current gas-liquid contact in the presence of an acidic or basic catalyst, to allow the two to react with each other, and withdrawing from the bottom a bottom stream containing a diol as major constituest; (b) continuously feeding to a hydrolyzer the distillate containing methyl acetate as major constituent obtained from said first reaction-distilling column, thus bringing said distillate into contact with water or steam in the presence of an acidic catalyst to effect hydrolysis, and (c) then continuously feeding the hydrolysis product from the hydrolyzer to a second distilling column, withdrawing a methyl acetate-containing methanol stream from the top of said second distilling column, and recycling said stream to the bottom of the first reaction-distilling column.

This invention is explained in detail below referring to the accompanying drawings, in which FIG. 1 is an x-y curve under atmospheric pressure showing the vapor-liquid equilibrium of a binary system of methyl acetate and methanol in the presence of 1,4-butanediol, FIG. 2 is an x-y curve under atmospheric pressure showing the vapor-liquid equilibrium of a binary system of methyl acetate and methanol in the presence of 2-butene-1,4-diol, and FIG. 3 shows the flow diagram of one of the Examples which appear hereinafter.

In FIG. 1, the dotted line refers to the x-y curve of a binary system consisting of methyl acetate and methanol, while the solid line refers to that of the above binary system in the presence of 50 mole% of 1,4-butanediol. In FIG. 2, the dotted line refers to the x-y curve of a binary system consisting of methyl acetate and methanol, while the solid line refers to that of the above binary system in the presence of 50 mole% of 2-butene-1,4-diol.

Methyl acetate and methanol are in such a vapor-liquid equilibrium as shown in FIG. 1 or 2 in the presence of a diol, and when the methyl acetate-containing methanol is fed to the bottom of the first reaction-distilling column, the vapor-liquid equilibrium takes place at only one stage (namely, single distillation), and hence, methyl acetate remains in the bottom stream. Therefore, it follows from reaction equilibrium that an ester of a diol is contained in the bottom stream and an extremely high purity diol cannot be obtained. Therefore, it is preferable to feed the methyl acetate-containing methanol to the column from a place above the bottom because, in this case, the vapor-liquid equilibrium takes place at two or more stages and hence the amount of methyl acetate remaining in the bottom stream becomes much smaller and an extremely high purity diol can be obtained. On the other hand, when the methyl acetate-containing methanol is fed to a place higher than the middle part of the column, the number of necessary plates of the whole column becomes larger and hence it is economically disadvantageous.

Therefore, the methyl acetate-containing methanol is preferably fed to the first reaction-distilling column from a place higher than the bottom but lower than the middle part of the column.

The diacetoxybutenes used as a starting material in this invention are obtained from butadiene, acetic acid and oxygen by catalytic reaction in the presence of, for example, a palladium-based catalyst and are converted into diacetoxybutanes by hydrogenation. These diol esters may be used alone or in admixture in the transesterification.

As the methanol which is another starting material, there is used the methyl acetate-containing methanol withdrawn from the top of the second distilling column where it is separated from the mixture obtained by hydrolysis of methyl acetate obtained as a by-product by the transesterification. The amount of the methyl acetate-containing methanol used may be varied depending upon the methyl acetate though it is generally suitable to feed the methyl acetate-containing methanol in such an amount that the amount of methanol becomes 1.0 to 5 moles, preferably 1.1 to 3.0 moles, per mole of the acetate group of the acetic ester of the diol. The allowable amount of methyl acetate in the methanol is 80 mole% or less, preferably 10 to 60 mole% based on the total amount of methanol and methyl acetate. If the methyl acetate content is too large, it is difficult to obtain a diol in a high yield. That the methanol containing such an amount of methyl acetate can be used without any obstruction in the transesterification similarly to the case of high-purity methanol is indeed unexpected and surprising. Moreover, regarding the material balance, by recycling the methyl acetate-containing methanol distilled out of the top of the second distilling column, it is possible to cover therewith 70% or more, even 90% or more under favorable conditions, of the total methanol to be fed to the first reaction-distilling column, and methanol separated by simple distillation from the bottom stream (comprising the objective diol as major constituent) of the first reaction-distilling column is sufficient enough to make up the balance, so that no fresh methanol is required to be fed. This brings about several advantages over the case of using high-purity methanol, such as saving of thermal energy, reduction in size of the distilling means, and so on.

When the starting material for the transesterification with methanol is diacetoxybutene, which is unsaturated, a basic catalyst is suitable and the use of an acidic catalyst is undesirable because there occur side reactions such as isomerization, and the like, whereas in the case of diacetoxybutene, which is saturated, either acidic or basic catalyst may be used. The acidic catalyst may be liquid or solid. The liquid acidic catalysts include inorganic acids such as sulfuric acid, phosphoric acid and the like, and organic acids such as benzenesulfonic acid, toluenesulfonic acids and the like. The solid acidic catalysts include acidic cation exchange resins, solid phosphoric acid, acid clay, silica-alumina, and the like. Among them, acidic cation exchange resins are generally used advantageously. The basic catalysts include sodium hydroxide, potassium hydroxide, sodium alkoxides, aluminum alkoxides, ammonia, pyridine, and the like, among which sodium hydroxide and potassium hydroxide are inexpensive and are generally used advantageously.

The amount of a catalyst used may be varied depending on its kind and cannot be standardized. When sodium hydroxide is used, if the catalyst concentration is too low, the reaction proceeds at a low rate and tends to terminate before completion, whereas if the concentration is too high, a large amount of undesirable salt is produced. Therefore, it is usually used in an amount of 0.1 to 10, preferably 0.2 to 5, mole% based on the acetic ester of diol. In the case of an acidic cation exchange resin, it is used in an acid equivalent corresponding to the concentration in which sodium hydroxide would be used. If the resin is used as a fixed bed in the reactor, the amount of the resin may be determined so as to meet the capacity of the reactor and the required contact time.

The first reaction-distilling column for the transesterification has such a function that methanol and an acetic ester of a diol are continuously fed to the column to subject them to gas-liquid contact with each other in the presence of an acidic or basic catalyst to allow them to react with each other and the methyl acetate produced as a by-product is, at the same time, continuously withdrawn as a distillate, and the column is preferably of the same type as a generally used distilling column. As the distilling column, there may be used a multiplate distilling column or a packed distilling column. The construction material may be varied depending upon the type of catalyst. When a basic catalyst is used, a steel of SS 41 grade is sufficient enough to stand the catalyst. In the case of an acidic catalyst, it is necessary to use a stainless steel of SUS 304 or SUS 316 grade or a glass-lined steel. The number of theoretical plates is 5 to 30. The operating pressure is not critical and may be atmospheric, or superatmospheric if necessary. The reflux ratio is usually 0 to 5. The reaction temperature depends on the bottom temperature. If the bottom temperature is too high, by-products such as cyclic ether and the like tend to be formed, whereas if it is too low, the methanol vapor will not ascend to a sufficient height, and hence, the column is not well operated. Therefore, a suitable bottom temperature is 70° to 180° C., preferably 75° to 150° C.

When subjecting to hydrolysis the mixture containing, as major constituent, methyl acetate which is the by-product of the transesterification, the amount of water or steam used depends upon the desired degree of hydrolysis of methyl acetate and cannot be generalized, though it is usually 1 to 20 moles per mole of methyl acetate. As the catalysts for the hydrolysis, similarly to those used in the transesterification, there may be used liquid acidic catalysts such as sulfuric acid, phosphoric acid, benzenesulfonic acid, toluensulfonic acids and the like; and solid acidic catalysts such as acidic cation exchange resins, solid phosphoric acid, acid clay, silica-alumina, and the like. The acidic cation exchange resin is generally used advantageously. When the acidic ion exchange resin is used as a fixed bed in a reactor, the amount of the resin used is determined so as to meet the capacity of the equipment and the required contact time.

The hydrolyzer has a function of hydrolyzing methyl acetate in the presence of an acidic catalyst, and its type may be that of a conventional stirring type reactor. If an acidic cation exchange resin is used as the catalyst, a tubular flow reactor is advantageous in view of protection of the catalyst from disintegration. If possible, the hydrolyzer may be incorporated into the second distilling column to carry out the hydrolysis and distillation in one step. Thus, the type of hydrolyzer is not critical. Although the capacity of the hydrolyzer may be varied depending on the reaction time and the kind of catalyst, the residence time of the methyl acetate-containing solution in the catalyst layer is usually in the range of 0.05 to 5 hours, preferably 0.1 to 2 hours. Since acetic acid is formed by hydrolysis, the construction material of the hydrolyzer is preferably a stainless steel of SUS 316 grade or a titanium-lined steel.

The second distilling column has a function of separating the methyl acetate-containing methanol from the aqueous acitic acid solution, and specifically, the column may be a distilling column generally used in distillation, and a multiplate distilling column or a packed distilling column may be used. The number of theoretical plates is 10 to 50. The operating pressure is not critical. The reflux ratio is usually 0.1 to 10, a reflux ratio of 0.1 to 3 being sufficient to achieve the purpose. Similarly to the case of hydrolysis, the construction material is preferably a stainless steel of SUS 316 grade or most preferably a titanium-lined steel, because the distillation is carried out in the presence of acetic acid.

The process of this invention is illustrated below in detail with reference to FIG. 3 in the accompanying drawings, in which I is a first reaction-distilling column; II a hydrolyzer; III a second distilling column; 1 the feed line for acetic ester; 2 the feed line for methanol mixture; 3 the discharge line for reaction product solution; 4 the outlet line for methyl acetate mixture; 5 the catalyst feed line; 6 the feed line for water (steam); 7 the hydrolyzate discharge line; 8 the aqueous acetic acid discharge line; and 9 the outlet line for methanol mixture.

The acetic ester of a diol is fed through the line 1 to the upper part of the first reaction-distilling column I while feeding through line 2 to the lower part the methyl acetate-containing methanol (if necessary, together with fresh methanol) that is the distillate of the second distilling column III, to counter-currently contact the ester with the methanol in the presence of the catalyst, thereby reacting the two. In this case, the method of feeding the catalyst may be varied depending upon the kind of catalyst. In the case of sodium hydroxide, it is dissolved in a portion of the reaction product solution containing the diol withdrawn from the line 5 or in fresh methanol, and the resulting solution is fed through the line 5 to the upper part of the first reaction-distilling column I. The reaction product solution obtained as the bottom stream through the line 3 is a methanol solution containing the diol as major constituent and substantially free from the unreacted acetic ester of the diol. Extremely high purity diol can be easily obtained from the reaction product solution by simple distillation (the methanol separated by distillation is combined with the recycled methyl acetate-containing methanol and is used in the transesterification). On the other hand, the methanol containing methyl acetate which flows out of the line 4 is mixed with water or steam supplied through the line 6 and is fed to the hydrolyzor II to undergo hydrolysis in the presence of an acid cation exchange resin used as the catalyst. The reaction mixture from the hydrolyzer II is a four-component mixture consisting of methyl acetate, methanol, water and acetic acid. This mixture is distilled in a usual way in the second distilling column III and the distillate from the line 9 containing methyl acetate and methanol is recycled to the first reaction-distilling column I to be used as a starting material for the transesterification. The bottom stream from the second distilling column III contains water and acetic acid. This mixture can be separated into water and acetic acid by subsequent treatments such as distillation and extraction.

As described in the foregoing, this invention provides a commercially advantageous and valuable method for the continuous production of a diol including the treatment of by-product, methyl acetate, by the transesterification between the acetic ester of the diol and methanol in the presence of an acidic or basic catalyst.

This invention is further illustrated below in detail with reference to Examples which are by way of illustration but not by way of limitation.

EXAMPLE 1

The first reaction-distilling column used was a distilling column made of stainless steel (SUS 316), 25 mm in inner diameter and 1,500 mm in height, packed with MacMahon packings made of stainless steel (SUS 316) and provided at the bottom with a 500-ml still equipped with a heating jacket. The hydrolyzer used was tubular flow reactor made of stainless steel (SUS 316), 50 mm in inner diameter and 700 mm in length, provided with a heat-insulating jacket, and packed with 1,300 ml of a commercially available acidic cation exchange resin (Amberite 200, a trademark), which had been converted to a sulfonic acid type by treating the same with hydrochloric acid, to serve as a catalyst bed. The second distilling column was a column made of stainless steel (SUS 316), 25 mm in inner diameter and 2,000 mm in height, provided with a heating jacket, packed with MacMahon packings (SUS 316), and provided at the bottom with a 500-ml still equipped with a heating jacket. The above means were connected through pumps, etc., as shown in the accompanying drawings, to carry out continuous reaction.

1,4-Diacetoxybutane was continuously fed at a rate of 522 g/hr through the line 1 to the first reaction-distilling column I via an inlet located at a distance of 100 mm below the top, while continuously feeding at a rate of 1,056 g/hr through the line 2 the distillate obtained from the second distilling column III to the column I via an inlet located at a distance of 400 mm above the bottom. A 2% sodium hydroxide solution in a portion of the bottom stream withdrawn from the first reaction-distilling column was fed as a catalyst at a rate of 130 g/hr through the line 5 to the first reaction-distilling column via an inlet located at a distance of 150 mm below the top. The still temperature of the column was maintained at 120° C. under atmospheric pressure and the reflux ratio was 0. The bottom stream was withdrawn at a rate of 293 g/hr through the line 3. The distillate was withdrawn at a rate of 1,288 g/hr through the line 4 and mixed with 827 g/hr of water supplied through the line 6. The mixture was preheated at 80° C. and fed continuously to the hydrolyzer II, wherein the temperature of the mixture was maintained at 80° C. to allow the reaction to proceed. The reaction mixture was fed continuously through the line 7 to the second distilling column III. The second distilling column III was continuously operated under atmospheric pressure at a reflux ratio of 1.5 and the bottom stream was withdrawn through the line 8 at a rate of 1,077 g/hr, while withdrawing the distillate through the line 9 at a rate of 1,037 g/hr. The distillate was mixed with a small quantity of methanol obtained by simple distillation of the bottom stream withdrawn through the line 3. The resulting mixture was recycled at a rate of 1,056 g/hr to the first reaction-distilling column. On distilling the bottom stream withdrawn through the line 3 after the removal of methanol, there was obtained 263 g/hr of 1,4-butanediol containing substantially no acetic ester.

In Table 1, there are summarized chemical compositions of various samples collected at several locations shown in accordance with numerical symbols in FIG. 3.

TABLE 1

| | | | | | | unit: mole % |
|---|---|---|---|---|---|---|
| Location | Methyl acetate | Water | Methanol | Acetic acid | 1,4-butanediol | Others |
| 2 | 45.0 | — | 55.0 | — | — | |
| 3 | — | — | 16.7 | — | 82.5 | Monohydroxy-monoacetoxy-butane: 0.8 Sodium acetate and sodium hydroxide: trace |
| 4 | 75.9 | — | 24.1 | — | — | |
| 7 | 14.1 | 60.5 | 16.4 | 9.0 | — | |
| 8 | — | 87.0 | — | 13.0 | — | |
| 9 | 46.3 | — | 53.7 | — | — | |

EXAMPLE 2

In the same manner as in Example 1, a continuous reaction-distillation experiment was run by using the apparatus described in Example 1, except that 1,4-diacetoxybutene-2 was substituted for the 1,4-diacetoxybutane, and fed at a rate of 516 g/hr.

The transesterification was carried out by continuously feeding the first reaction-distilling column I with 1,4-diacetoxybutene-2, the distillate obtained from the second distilling column III, and sodium hydroxide dissolved in a portion of the reaction product solution. The bottom stream was withdrawn at a rate of 287 g/hr. The distillate was withdrawn at a rate of 1,289 g/hr, then mixed with 827 g/hr of water and fed to the hydrolyzer II after having been preheated at 80° C. The hydrolyzate was fed as such to the second distilling column III. The bottom stream was withdrawn from the column III at a rate of 1,077 g/hr. The distillate was mixed with a small quantity of methanol obtained by simple distillation of the bottom stream withdrawn through the line 3, and the resulting mixture was recycled at a rate of 1,057 g/hr to the first reaction-distilling column I. On distillation of the bottom stream withdrawn through the line 3 from which methanol had been removed, there was obtained 254 g/hr of 2-butene-1,4-diol substantially free from acetic ester.

In Table 2, there are summarized chemical compositions of various samples collected at several locations shown in accordance with numerical symbols in FIG. 3.

TABLE 2

| | | | | | unit: mole % | |
|---|---|---|---|---|---|---|
| Location | Methyl acetate | Water | Methanol | Acetic acid | 2-Butene-1,4-diol | Others |
| 2 | 45.0 | — | 55.0 | — | — | |
| 3 | — | — | 16.8 | — | 82.7 | Monohydroxy-monoacetoxy-butene: 0.5; sodium hydroxide acetate: trace |
| 4 | 76.0 | — | 24.0 | — | — | |
| 7 | 14.1 | 60.5 | 16.4 | 9.0 | — | |
| 8 | — | 87.0 | — | 13.0 | — | |
| 9 | 46.4 | — | 53.6 | — | — | |

COMPARATIVE EXAMPLE 1

In the same apparatus as in Example 1, 1,4-diacetoxybutane was continuously fed to the first reaction-distilling column I at a rate of 522 g/hr from a location 100 mm below the top through the feed line 1, and the distillate obtained from the second distilling column was simultaneously continuously fed to the still (bottom) of the first reaction-distilling column I at a rate of 1,061 g/hr through the feed line 2, and the other conditions were the same as in Example 1, to continuously operate the apparatus. The bottom stream was taken out at a rate of 317 g/hr through the line 3, and the distillate was withdrawn at a rate of 1,269 g/hr through the line 4 and then fed to the hydrolyzer along with 721 g/hr of water obtained through the line 6. The reaction mixture in the hydrolyzer was fed as obtained to the second distilling column III, and the bottom stream was taken out at a rate of 953 g/hr, while the distillate was combined with a small amount of methanol obtained by simple distillation from the bottom stream from the line 3, and the combined stream was fed to the still (bottom) of the first reaction-distilling column at a rate of 1,061 g/hr.

From the bottom stream obtained from the line 3, a small amount of methyl acetate and methanol were removed, and the residual liquid was distilled to obtain 1,4-butanediol containing about 20 mole% of the acetic ester of the diol at a rate of 286 g/hr.

The compositions of samples in main locations were as shown in Table 3 in accordance with the numerical symbols in FIG. 3.

TABLE 3

| Location | Methyl acetate | Water | Methanol | Acetic acid | 1,4-Butanediol | Others |
|---|---|---|---|---|---|---|
| 2 | 45.6 | — | 54.4 | — | — | |
| 3 | 3.3 | — | 13.3 | — | 66.7 | Monohydroxy-monoacetoxybutane: 16.7 Sodium acetate and sodium hydroxide: trace |
| 4 | 72.7 | — | 27.3 | — | — | |
| 7 | 15.4 | 58.1 | 17.8 | 8.7 | — | |
| 8 | — | 87.0 | — | 13.0 | — | |
| 9 | 46.3 | — | 53.7 | — | — | | unit: mole %

What is claimed is:

1. A process for producing a diol by reacting an acetic ester of butanediol or butenediol with methanol, which comprises (a) continuously feeding to a first reaction-distilling column from an upper part thereof a liquid acetic ester of a butanediol or butenediol, while continuously feeding methanol to the said column from a place higher than the bottom but lower than the middle part thereof, to bring both feeds into counter current gas-liquid contact in the presence of an acidic or basic catalyst, thereby allowing both feeds to react, withdrawing from the bottom a bottom stream containing a diol as major constituent, (b) continuously feeding to a hydrolyzer the distillate which is obtained from said first reaction-distilling column and which contains methyl acetate as major constituent, thus bringing said distillate into contact with water or steam in the presence of an acidic catalyst to effect hydrolysis, (c) then continuously feeding the reaction mixture from the hydrolyzer to a second distilling column, withdrawing a methyl acetate-containing methanol stream from the top of the second distilling column, and recycling said stream to a place higher than the bottom but lower than the middle part of the first reaction-distilling column, wherein the amount of methanol fed to a place higher than the bottom but lower than the middle part of the first reaction-distilling column is 1.0 to 5 moles per mole of the ester group of the acetic ester of diol.

2. A process according to claim 1, wherein the methanol fed to a place higher than the bottom but lower than the middle part of the first reaction-distilling column contains 70% or more, based on the total amount of methanol fed, of the distillate from the top of the second distilling column.

3. A process according to claim 1, wherein the methyl acetate content in the methanol fed to a place higher than the bottom but lower than the middle part of the first reaction-distilling column is 80 mole % or less based on the total sum of methanol and methyl acetate.

4. A process according to claim 3, wherein the methyl acetate content is 10 to 60 mole%.

5. A process according to claim 1, wherein the acidic catalyst for the hydrolysis is a liquid acid selected from the group consisting of sulfuric acid, phosphoric acid, benzenesulfonic acid and toluenesulfonic acids.

6. A process according to claim 1, wherein the acidic catalyst for the hydrolysis is a solid acid selected form the group consisting of acidic cation exchange resins, solid phosphoric acid, acid clay and silica-alumina.

7. A process according to claim 1, wherein the acidic catalyst for the hydrolysis is an acidic cation exchange resin.

8. A process according to claim 1 or 5, wherein the residence time in the catalyst layer of the feed passing through the hydrolyzer is 0.05 to 5 hours.

9. A process according to claim 1 or 5, wherein the residence time in the catalyst layer of the feed passing through the hydrolyzer is 0.1 to 2 hours.

10. A process according to claim 1, wherein the second distilling column has a number of theoretical plates of 10 to 50 and the reflux ratio is 0.1 to 10.

11. A process according to claim 1, wherein the amount of water or steam used in the hydrolysis is 1 to 20 moles per mole of methyl acetate.

12. A process according to claim 1, wherein the number of theoretical plates in the first reaction-distilling column is 5 to 30, the reflux ratio in the first reaction-distilling column is 0 to 5, and the bottom temperature in the first reaction-distilling column is 70° to 180° C.

13. A process according to claim 1, wherein the amount of methanol fed to a place higher than the bottom but lower than the middle part of the first reaction-distilling column is 1.1 to 3 moles per mole of the ester group of the acetic ester of diol.

14. A process according to claim 1, wherein the catalyst used in the first reaction-distilling column is a liquid acid selected from the group consisting of sulfuric acid, phosphoric acid, benzenesulfonic acid, and toluenesulfonic acids.

15. A process according to claim 1, wherein the catalyst used in the first reaction-distilling column is a solid acid selected from the group consisting of acidic cation exchange resins, solid phosphoric acid, acid clay, and silica-alumina.

16. A process according to claim 1, wherein the catalyst used in the first reaction-distilling column is an acidic cation exchange resin.

17. A process according to claim 1, wherein the catalyst used in the first reaction-distilling column is a basic catalyst selected from sodium hydroxide, potassium hydroxide, sodium alkoxides, aluminum alkoxides, ammonium, and pyridine.

18. A process according to claim 1, wherein the catalyst used in the first reaction-distilling column is sodium hydroxide or potassium hydroxide.

19. A process according to claim 1, wherein the amount of the catalyst used in the first reaction-distilling column is 0.1 to 10 mole% based on the amount of the acetic ester of diol.

20. A process according to claim 1, wherein the amount of the catalyst used in the first reaction-distilling column is 0.2 to 5 mole% based on the total amount of the acetic ester of diol.

* * * * *